(12) United States Patent
Larson et al.

(10) Patent No.: US 6,874,699 B2
(45) Date of Patent: Apr. 5, 2005

(54) METHODS AND APPARATA FOR PRECISELY DISPENSING MICROVOLUMES OF FLUIDS

(75) Inventors: Bradley James Larson, Madison, WI (US); Chung Hoon Lee, Ithaca, NY (US); Amit Lal, Ithaca, NY (US); Max G. Lagally, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/271,250

(22) Filed: Oct. 15, 2002

(65) Prior Publication Data

US 2004/0071601 A1 Apr. 15, 2004

(51) Int. Cl.[7] .................................................. B05B 1/08
(52) U.S. Cl. ............................... 239/102.1; 239/102.2; 239/86; 239/589.1; 422/100; 422/930; 73/1.74; 73/863.32; 73/864.01; 73/864.22; 347/46; 347/47
(58) Field of Search ........................... 239/102.1, 102.2, 239/86, 589.1; 427/600; 422/100, 930; 435/286.3, 286.4; 73/1.74, 863.32, 864.01, 864.22; 222/36–38, 55, 57, 420, 422; 347/46, 47

(56) References Cited

U.S. PATENT DOCUMENTS

| | | | |
|---|---|---|---|
| 4,877,745 A | 10/1989 | Hayes et al. ............... 436/166 |
| 5,558,837 A * | 9/1996 | Tsukishima ................ 422/99 |
| 5,658,802 A | 8/1997 | Hayes et al. ............... 436/518 |
| 5,707,588 A * | 1/1998 | Tsukishima ................ 422/99 |
| 5,927,547 A | 7/1999 | Papen et al. ............... 222/57 |
| 5,962,329 A * | 10/1999 | Ershov et al. .............. 436/50 |
| 6,001,309 A | 12/1999 | Gamble et al. ............. 422/100 |
| 6,079,283 A | 6/2000 | Papen et al. ............. 73/864.11 |
| 6,083,762 A | 7/2000 | Papen et al. ............... 436/180 |
| 6,094,966 A | 8/2000 | Papen et al. ................ 73/1.74 |
| 6,106,635 A * | 8/2000 | Hamada et al. ............. 134/33 |
| 6,112,605 A | 9/2000 | Papen et al. ............. 73/864.22 |
| 6,203,759 B1 | 3/2001 | Pelc et al. ................ 422/100 |
| 6,220,075 B1 | 4/2001 | Papen et al. ................ 73/1.74 |
| 6,223,996 B1 * | 5/2001 | Yamamoto ............... 239/102.2 |
| 6,232,129 B1 | 5/2001 | Wiktor ..................... 436/180 |
| 6,296,811 B1 | 10/2001 | Sasaki ..................... 422/100 |
| 6,387,330 B1 | 5/2002 | Bova et al. ................ 422/100 |
| 6,416,164 B1 | 7/2002 | Stearns et al. .............. 347/46 |
| 6,422,431 B2 | 7/2002 | Pelc et al. ................. 222/422 |
| 6,638,249 B1 * | 10/2003 | Lal et al. .................. 604/151 |
| 6,669,103 B2 * | 12/2003 | Tsai ........................... 239/4 |

OTHER PUBLICATIONS

Ultrasonics Theory (http://www.variclean.nl/theory.html).*
HELA Local Authority Circular (LAC No. 59/1, Oct. 2000, http://www.hse.gov.uk/lau/lacs/59–1.htm).*

* cited by examiner

Primary Examiner—Thomas Denion
Assistant Examiner—Kyle M. Riddle
(74) Attorney, Agent, or Firm—Craig A. Fieschko, Esq.; DeWitt Ross & Stevens S.C.

(57) ABSTRACT

Devices and methods for depositing fluids on substrates in patterns of spots, lines, or other features use a nozzle, which is preferably configured similarly to a micropipette, having a piezoelectric crystal or other ultrasonic actuator coupled to one of its sides. The nozzle may be charged via capillary action by dipping it into a well containing the fluid to be deposited, and may then be positioned over a desired area of a substrate, at which point activation of the ultrasonic actuator at ultrasonic frequencies will eject the fluid onto the substrate. The needle may subsequently be dipped into a well of rinsing fluid for cleaning. Spots or lines on the order of 5 micrometers width may be generated, making the invention particularly suitable for use in biological applications such as microarray production and in microelectronics applications such as the printing of organic circuitry.

20 Claims, 1 Drawing Sheet

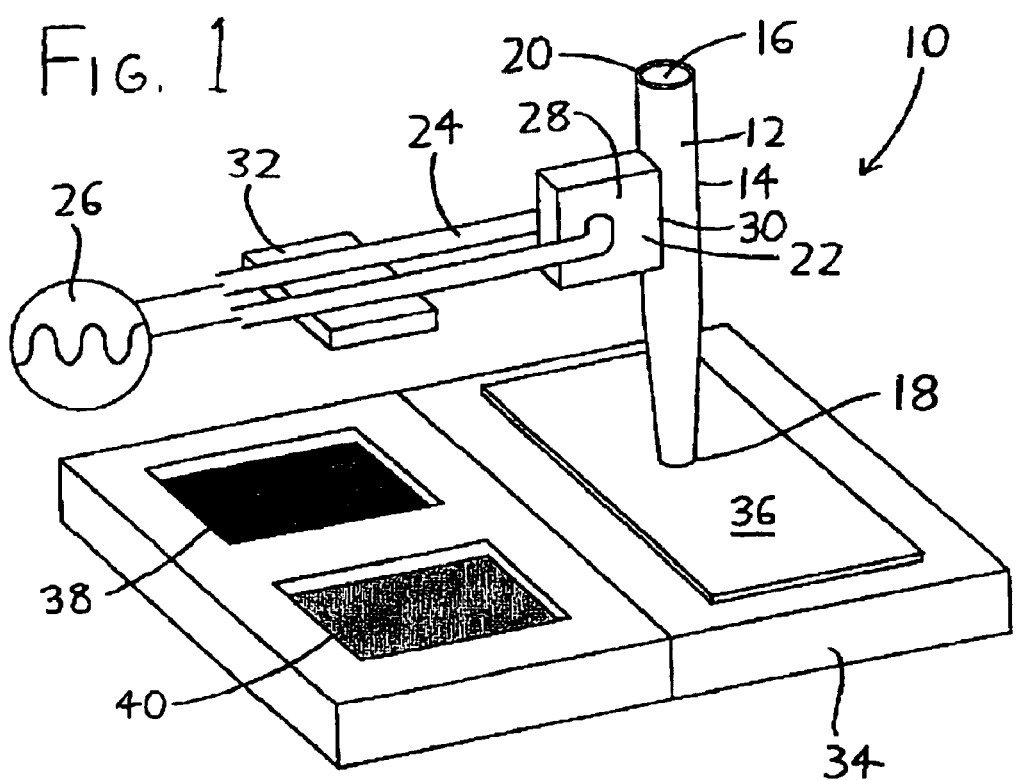

METHODS AND APPARATA FOR PRECISELY DISPENSING MICROVOLUMES OF FLUIDS

STATEMENT REGARDING FEDERALLY SPONSORED RESEARCH

This invention was made with United States government support awarded by National Science Foundation Grant No. NSF 9725021. The United States has certain rights in this invention.

FIELD OF THE INVENTION

This document concerns an invention relating generally to methods and apparata for dispensing microvolumes of fluids, and more specifically to methods and apparata for depositing very small spots, lines, or other desired patterns of fluids on substrates.

BACKGROUND OF THE INVENTION

In the fields of biotechnology and nanotechnology, it is often useful to precisely dispense very small desired quantities of fluids in some desired pattern on a substrate. As an example, in the field of nanotechnology, it can be useful to situate lines or other patterns of catalysts or nucleation agents on a substrate to ready it for the later growth or deposition of other materials at these sites. As another example, in the field of biotechnology, it is often useful to situate arrays of "spots" of oligonucleotides on glass slides or other substrates for use in the later analysis of nucleic acid sequences. At the time this document was prepared, some microarray spotters are able to accomplish spot sizes on the order of 75 micrometers using dispensation methods such as the use of quill pens. However, quill pen dispensation suffers from the disadvantage that over time, as quill tips (which can cost as much as several hundred dollars per tip) degrade, spot sizes grow and become more irregular. Additionally, while the ability to generate spots having diameters on the order of 75 micrometers is useful for applications such as generation of biological microarrays, the ability to generate still smaller spot sizes would be valuable.

Other exemplary apparata for dispensation of microvolumes of fluids are described in U.S. Pat. Nos. 6,220,075, 6,112,605, 6,083,762, 6,079,283, and 5,927,547 to Papen et al.; U.S. Pat. Nos. 5,658,802 and 4,877,745 to Hayes et al.; U.S. Pat. No. 6,232,129 to Wiktor; and U.S. Pat. No. 6,296,811 to Sasaki. As these patents illustrate, a common arrangement used for fluid microvolume dispensation is to provide an elongated nozzle (e.g., a pipette or other tube) which has a piezoelectric tube or ring element surrounding at least a portion of its length. The piezoelectric tube/ring is situated between the dispensing end of the nozzle (the end from which fluid is to be dispensed), and an opposing end which is usually attached to a fluid supply via rigid or flexible tubing. The dispensing end of the nozzle is situated slightly above the substrate upon which fluid is to be deposited. The piezoelectric tube/ring is then powered at frequencies generally ranging in the sonic (less than 20 kHz) or ultrasonic ranges, and at amplitudes ranging from 20–150V; see, e.g., U.S. Pat. No. 6,232,129 at column 5 lines 28–35, and/or U.S. Pat. No. 6,296,811 at column 5 lines 23–33. The piezoelectric tube/ring then expands and contracts at this excitation frequency, resulting in corresponding expansion and contraction of the interior of the piezoelectric tube/ring, and thus the adjacent nozzle walls which the tube/ring surrounds. Fluid resting within the nozzle is then expelled from the nozzle's dispensing end by what appears to be an action similar to peristaltic pumping, with the opposite end of the nozzle being supplied with further fluid from the fluid supply. By use of this arrangement, dispensation of microvolumes as small as 10 picoliters (0.01 nanoliters) is reported (see, e.g., U.S. Pat. No. 6,296,811 at column 5 line 51 onward). This corresponds to spot sizes as small as approximately 35 micrometers in diameter, assuming an aqueous solution is deposited on a glass slide (which is moderately hydrophilic).

Arrangements of this nature can also be used for fluid aspiration (fluid removal) rather than fluid dispensing. U.S. Pat. No. 6,232,129 notes (at column 5 line 56-column 6) that a nozzle can be used to aspirate fluid from a fluid supply by inserting an empty nozzle's dispensing end within a fluid supply and actuating the piezoelectric tube/ring. It appears that when the piezoelectric ring/tube is vibrated, any fluid flows in the nozzle in the direction of least resistance/lower pressure (i.e., from within the fluid collected within the nozzle to the atmosphere when dispensing, or from the fluid supply to the empty interior of the nozzle when aspirating).

An apparently different form of vibrational aspiration is described in U.S. patent application Ser. No. 09/617,479 (now U.S. Pat. No. 6,638,249), naming inventors Amit Lal and Chung-Hoon Lee and assigned to the assignee of the present invention. This document describes improved hypodermic-type needles wherein an outer needle having a sharpened end may be inserted within a body, and an inner tube situated within the outer needle may be ultrasonically vibrated to aspirate fluid from the outer needle (and thereby cause the outer needle to aspirate fluid from the body). The inner tube rests atop a silicon horn which is in turn coupled to an ultrasonic actuator driven at 100 kHz–1 megahertz or higher. The born is connected to a frame which bears the outer needle in a manner such that transmission of vibrations to the outer needle is minimized. The arrangement is somewhat bulky owing to the need to mount die inner needle within tie outer needle in such a manner that vibrational coupling between the two is minimized.

A disadvantage of the prior piezoelectric ring/tube nozzles is their size, complexity, and cost. Cost and complexity are issues owing to the need to manufacture a piezoelectric tube/ring wherein a nozzle can be inserted with close coupling between the structures. Size is problematic since it will often be useful to provide multiple adjacent nozzles which dispense onto the same substrate (each often depositing a different fluid), thereby allowing rapid dispensation of multiple spots or other features. However, looking to nozzle arrangements such as those shown in FIG. 1 of U.S. Pat. No. 6,232,129, and FIG. 2 of U.S. Pat. No. 6,001,309, there are apparent difficulties in providing such nozzles sufficiently closely spaced in an array that they can be simultaneously used to dispense fluids on the same small substrate (e.g., on the same microarray slide). Additional difficulties would be encountered with nozzle arrays because the size of deposited spots may vary in accordance with the distance of the dispensing end of each nozzle from the substrate, and if the heights of the various nozzles are not precisely aligned so that their dispensing ends are spaced at the same distance from the substrate's surface, the spot sizes produced by the various nozzles will vary. It might instead be possible to use only a single nozzle to sequentially deposit different fluids on a substrate, with the nozzle being interchanged between fluids (and rinsed between changes), but this approach leads to a significant increase in process time and can also result in unnecessary waste where the fluid being deposited is scarce.

The piezoelectric ring/tube arrangement also has the disadvantage that fluid dispensation/aspiration will not be effective unless the nozzle is "primed" with fluid to such a height that the fluid rests at or near the level of the piezoelectric ring/tube, else the expansion and contraction of the piezoelectric ring will not successfully enable pumping (see, e.g., U.S. Pat. No. 6,232,129 at column 5 line 36 onward). This implies that the foregoing arrangements may be unsuitable for use in microdispensation of fluids which are only available in extremely limited quantities, since the nozzle may need to be supplied with more fluid than is intended for dispensation owing to the need to prime the nozzle.

SUMMARY OF THE INVENTION

The invention, which is defined by the claims set forth at the end of this document, is directed to methods and apparata which at least partially alleviate the aforementioned problems. A basic understanding of some of the preferred features of the invention can be attained from a review of the following brief summary of the invention, with more details being provided elsewhere in this document.

Preferred versions of the invention include a fluid dispensation apparatus having a dispensing nozzle with an outer surface which circumferentially surrounds an interior passage, with the interior passage extending along a passage axis between a dispensing end and an opposite end. The dispensing nozzle may take the form of a capillary or similar small-diameter tube, and most preferably takes the form of a needle-like tube wherein the area of the interior passage at the dispensing end is smaller than the area of the interior passage at the opposite end.

An ultrasonic actuator such as a piezoelectric element is then coupled to a portion of the nozzle's circumference, as by simply bonding the ultrasonic element onto the outer surface of the nozzle so that it extends from a portion of the outer surface's circumference. The ultrasonic actuator therefore does not encircle the nozzle and compress it about its circumference when actuated. The power leads for the ultrasonic actuator may be provided in the form of conducting leads (such as insulated or uninsulated wires) which extend from the ultrasonic actuator, and which serve as the support for the nozzle to maintain it in a desired location. If elastically flexible conducting leads support the nozzle, they may usefully serve as an elastic mount for the nozzle which will yield if the nozzle is advanced against a substrate or other object, and which will also help to damp vibrations from the nozzle (and its ultrasonic actuator) to the surrounding structure.

A first fluid supply well containing a first fluid to be dispensed by the nozzle, and also preferably a second fluid supply well containing a rinsing fluid, may then be provided in conjunction with the nozzle so that the nozzle may be charged with the first fluid and/or rinsed with the rinsing fluid. A positioning stage, which preferably includes at least one coarse positioner (which may take the form of linear and/or rotary actuators such as screw drives, stepper motors, etc.) and one fine positioner (which preferably takes the form of a piezoelectric nanopositioner or the like), may then be interposed between the nozzle and the first and/or second fluid supply wells. The positioning stage allows the nozzle to be moved from some operating position to access the first fluid supply well (and second fluid supply well, if present) to receive fluid. Most preferably, the nozzle is sized and configured such that if its dispensing end is situated within the first and/or second fluid supply wells, fluid will be drawn into the dispensing end and into the nozzle's interior passage via capillary action.

A substrate mount is then provided for receiving a substrate upon which the first fluid is to be deposited by the nozzle. For example, when the fluid deposition apparatus is to be used as a microarray spotter, the substrate mount can be configured to receive and hold glass slides, membranes, or other substrates upon which the first fluid is to be deposited. Alternatively, the substrate mount may itself be the substrate, e.g., it may simply consist of a glass slide or the like having surfaces at which the first fluid is to be deposited. The substrate mount can also include (or may itself be no more than) a positioning stage to allow any substrate provided thereon to be positioned as desired, The positioning stage(s) may then situate the nozzle dispensing end adjacent to the substrate mount to allow the first fluid to be ejected from the interior passage of the nozzle and the nozzle's dispensing end, and toward the substrate mount, when the ultrasonic actuator is activated to vibrate at appropriate frequencies. The ultrasonic actuator may be intermittently actuated as the nozzle is moved relative to the substrate mount, thereby forming spaced discrete deposits of the first fluid. An exemplary application of this methodology is in the field of microarray manufacture for gene expression analysis, wherein one or more oligonucleotides may be deposited in an array of very small spots about the surface of a substrate. Alternatively, the ultrasonic actuator may be continuously actuated as the nozzle is moved relative to the substrate mount, thereby forming lines or other shaped deposits of the first fluid. Here, an exemplary application of the invention is in the field of microcircuit processing, where a catalyst or nucleation agent for the growth or later deposition of a desired material may be applied to a substrate in a desired pattern. In any event, it should be understood that the positioning stage may adjust the location of the nozzle relative to the substrate mount, and to the first fluid supply well and second fluid supply well (if any), by moving the nozzle with respect to a stationary mount and fluid supply well(s); by moving the mount (and fluid supply wells, if any) with respect to a stationary nozzle; or by some combination of these arrangements, wherein both the nozzle and mount/fluid supply wells might each translationally and/or rotationally move in at least some selected dimensions. Additionally, it should be understood that more than one fluid supply well (and more than one fluid) may be provided so that different fluids may be charged into and ejected from the nozzle. To prevent cross-contamination between fluid supply wells, the second fluid supply well and its rinsing fluid (if provided) may be used between one or more events of fluid dispensation onto the substrate.

The foregoing apparatus and methodology yields numerous advantageous results. Initially, the apparatus is capable of achieving exceptionally small and regular spot (or line) sizes for deposited fluids. To illustrate, versions of the apparatus were constructed using a pulled pipette (having an inner diameter of approximately 0.1 micrometer at the dispensing end) as a nozzle. When the nozzle was charged with an aqueous test solution such as food coloring and excited at above 250 kHz (preferably at 500–800 kHz), spots on the order of 20 micrometers in diameter were formed on a glass slide substrate situated adjacent to the dispensing end. Different fluids and substrates may achieve even smaller deposits, with spot sizes as low as approximately 5 micrometers being achieved when an aqueous solution was deposited on a hydrophobic surface.

Additionally, the apparatus is significantly less expensive to construct than prior ring-type ultrasonic nozzles, which require precise tolerances to successfully fit their piezoelectric rings about their needles: nozzles can be constructed by simply dicing piezoelectric material using a dicing saw, soldering spaced leads onto a diced element, and bonding the element to a pulled glass pipette or other capillary-type element. The nozzles can easily be formed at costs allowing disposable use, with production and materials costs in prototype nozzles being less than a dollar per unit (as of the year 2002).

Further, the ability to place the ultrasonic actuator about only a portion of the circumference of the nozzle, rather than about the entirety of the circumference of the nozzle's outer diameter, is believed to allow for charging of the nozzle with smaller and more exact quantities of fluid. It is believed that ring/tube-type ultrasonic nozzles generally have greater inner passage diameters (being at least multiple micrometers wide) owing to the need to successfully manufacture a nozzle with a surrounding piezoelectric ring/tube. It is also believed that the ring/tube-type nozzles operate best when charged with fluid within the interior passage of the nozzle to a point where the fluid level rests above the piezoelectric ring/tube, with performance deteriorating as the fluid level drops below the ring since the peristaltic-type pumping action becomes more difficult to maintain. As a result, such nozzles require a fluid charge having some minimum volume for effective performance, whereas the nozzles of the present invention have not been found to have lower boundaries on the volumes of charges they may accommodate. Additionally, prior nozzles are generally charged by having supply tubing supply fluids to their ends opposite their dispensing ends, and this "top filling" can lead to waste of the fluid left over in the tubing and nozzle when dispensation operations are ceased (e.g., when a manufacturing run is completed or when switching between fluids). In contrast, the nozzles of the present invention can have significantly smaller diameter, and can be accurately charged with minimal amounts of fluid (if desired) by simply dipping their dispensing ends within the desired fluid supply well and allowing the nozzle to be charged by fluid uptake through capillary action. There is no need to fill the entire nozzle, nor is there a need to fill it to at least the level at which the ultrasonic actuator is mounted; instead, the nozzle only need be charged with the amount of fluid desired for dispensation, which can lead to significantly less waste when expensive and difficult to synthesize fluids are involved.

Another advantage is provided where the conducting leads for the ultrasonic actuator are used to support the nozzle with respect to the substrate. Since the leads may provide a flexible mount for the nozzle, allowing the dispensing end of the nozzle to advance into contact with the substrate (with further advancing of the nozzle simply resulting in elastic yielding of the leads), the leads provide an advantageous means of accommodating imprecise spacing of the nozzle's dispensing end from the substrate (which is often encountered owing to variations in the substrate's height across its surface). Since the apparatus is capable of depositing fluid even when the nozzle's dispensing end is in contact with a surface, one can be assured of at least relatively uniform spot sizes between successive deposition events by simply advancing the nozzle's dispensing end onto the surface of the substrate during each event.

Further advantages, features, and objects of the invention will be apparent from the following detailed description of the invention in conjunction with the associated drawings.

BRIEF DESCRIPTION OF THE DRAWINGS

FIG. 1 is a simplified perspective diagram illustrating an exemplary version of the apparatus of the invention.

DETAILED DESCRIPTION OF PREFERRED VERSIONS OF THE INVENTION

Referring to FIG. 1, an exemplary version of an apparatus for dispensing microvolumes of fluid onto a substrate is overall designated by the reference numeral 10. The apparatus 10 includes an elongated nozzle 12 bounded on its exterior by a nozzle outer surface 14, and bounded on its interior by a nozzle interior passage 16, which extends between a nozzle dispensing end 18 and an opposite end 20. The dispensing end 18 is preferably narrowed in comparison to the opposite end 20 so that the area of the interior passage 16 is smaller at the dispensing end 18 than at the opposite end 20.

While it is expected that the nozzles 12 could be formed with a variety of different materials using a number of different techniques, the dispensing nozzle 12 may be manufactured particularly inexpensively using a standard micropipette puller, which heats and elongates glass tubes to attain microcapillaries of desired sizes. Glass nozzles 12 of this nature having interior passages 16 with diameters between 0.1 micrometer–1 micrometer have been successfully tested in the invention, though it is expected that nozzles 12 having different inner diameters, perhaps as well as nozzles having nonsymmetrical configurations (e.g., nozzles having triangular, square or other diagonal cross sections), might be successfully used.

For reasons to be discussed in greater detail below, it is particularly preferred that the nozzle 12 be sized, configured, and formed of materials such that the nozzle 12 is capable of drawing in the fluid(s) to be dispensed by the nozzle 12 via capillary action if the dispensing end 18 is inserted into the fluid supply. The nozzle's opposite end 20 is therefore preferably left open to the atmosphere so that the intake of fluid to nozzle interior passage 16 will not be hindered by air pressure within the interior passage 16 of nozzle 12 at the opposite end 20.

An ultrasonic actuator 22 is coupled to a portion of the circumference of the nozzle outer surface 14. The ultrasonic actuator 22 may simply take the form of a diced piece of piezoelectric material which is bonded to the nozzle outer surface 14 via an isocyanate-based bonding agent or any other suitable adhesive. Since the ultrasonic actuator 22 is affixed about a portion of the circumference of the nozzle outer surface 14, the nozzle 12 does not pump fluid via a peristaltic-type constriction and expansion of the diameter of the nozzle 12 (as is common in prior arrangements).

Conducting leads 24 are connected to the ultrasonic actuator 22 in spaced relationship to allow expansion and contraction of the ultrasonic actuator 22 when appropriately powered by a signal generator (such a signal generator being depicted schematically in FIG. 1 at 26). The conducting leads 24 in FIG. 1 are depicted as extending from opposing sides 28 of the ultrasonic actuator 22 so that the leads 24 generally extend from a plane perpendicular to the passage axis of the nozzle interior passage 16, with the nozzle 12 being bonded to a mounting side 30 of the ultrasonic actuator 22 which rests between the sides 28 from which the leads 24 extend. This arrangement is particularly preferred because if the conducting leads 24 are flexible, and if they define the only support for the nozzle 12, the conducting leads 24 will effectively define a flexible mount for the nozzle 12 which will allow it to elastically yield if the dispensing end 18 of the nozzle 12 is advanced onto the surface of a substrate or other object.

The signal generator 26 used to excite the ultrasonic actuator 22 may take the form of a standard oscillator/function generator capable of supplying sinusoidal or similar waveforms (e.g., square, triangular, or sawtooth waveforms) at ultrasonic frequencies preferably ranging between 250–800 kHz, with voltages preferably ranging between 1–10 volts (peak to peak), when used in conjunction with nozzles 12 having the aforementioned dimensions. However, it should be understood that other frequency ranges and voltages may be appropriate for nozzles 12 having other dimensions.

An optional nozzle positioning stage 32 is then schematically depicted in FIG. 1 on the conducting leads 24. Actuation of the positioning stage 32 may allow motion of the conducting leads 24 (and thus the nozzle 12) in one or more dimensions as a user desires for positioning of the nozzle dispensing end 18 at a desired location. The positioning stage 32 may take the form of any number of actuators known in the art (e.g., worm screw positioners, electromagnetic actuators, piezoelectric actuators, etc.). A particularly preferred positioning stage includes a combination of a coarse positioning actuator (such as a worm screw) coupled to a fine positioning actuator (such as a piezoelectric nanopositioner), thereby providing the nozzle 12 with a wide but precisely controllable range of motion.

A substrate mount 34 suitable for receiving a substrate 36 is then provided at a location whereby the nozzle dispensing end 18 may be situated adjacent to substrate 36 to allow fluid to be dispensed thereon. The substrate mount 34 may itself be provided by a positioning stage in addition to (or instead of) any positioning stage 32 provided for the nozzle 12, thereby allowing positioning of the substrate 36 in one or more dimensions as the user desires. It is noted that the substrate mount 34 may itself be the substrate 36, i.e., the surface over which the nozzle 12 is situated may receive fluid ejected from the nozzle 12 without prior placement of a different substrate 36 thereupon.

A fluid supply well 38 is preferably provided in a location accessible to the nozzle dispensing end 18, whereby the nozzle dispensing end 18 may be inserted into the fluid supply well 38 to allow the nozzle 12 to be charged with the fluid therein (as previously noted, preferably by simply allowing fluid uptake from the nozzle interior passage 16 via capillary action). If the nozzle positioning stage 32 is incapable of placing the nozzle 12 within the fluid supply well 38 (or if the nozzle positioning stage 32 is not provided), the fluid supply well 38 may itself be defined within or upon a positioning stage to allow the fluid supply 38 to be moved to the location of the nozzle 12. The fluid supply well 38 is intended to hold the fluid which is intended to be deposited on the substrate 36, and thus might hold a solution containing biological probes, nucleating agents, or other substances.

It is also useful to provide a second fluid supply well 40 which contains a rinsing fluid, such as deionized water, for cleaning the nozzle 12 and its interior passage 16 as desired (a process which will be described at greater length below). Like the first fluid supply well 38, the second fluid supply well 40 may be defined within or upon a positioning stage to allow it to be moved to the location of nozzle 12.

The following process may be used to dispense fluid onto a substrate 36. The substrate 36 is loaded onto the substrate mount 34, with the surface upon which the fluid is to be dispensed located in a position reachable by the nozzle dispensing end 18 when the substrate 36 and/or the nozzle 12 are appropriately positioned by their respective positioning stages 32 and 34 (with only one positioning stage being used if both are not present). The nozzle 12 is then positioned so that its nozzle dispensing end 18 may be inserted into the first fluid supply well 38, which contains the fluid to be dispensed onto the substrate 36. Again, such positioning may be done by moving the nozzle 12 and/or the first fluid supply well 38 by their respective positioning stages (if present). The nozzle dispensing end 18 is then inserted within the first fluid supply well 38 to draw the fluid contained within the first fluid supply well 38 into the nozzle interior passage 16 via capillary action. The nozzle 12 may simply be left within the first fluid supply well 38 until capillary filling ceases, with such filling being dependent on factors such as how deeply the nozzle 12 is inserted within the first fluid supply well 38, the properties of fluid within the first fluid supply well, and the properties and sizing/configuration of the nozzle 12. An advantage of using capillary action for charging of the nozzle 12 as opposed to some other forced means of charging (e.g., application of a pressure differential across the ends of the nozzle 12) is that capillary action allows for controlled uptake of fluid, and allows the nozzle 12 to be removed from the first fluid supply well 38 at such a time that a desired amount of fluid is received within the nozzle interior passage 16. Thus, the nozzle interior passage 16 might only be charged with a precise amount of fluid desired for dispensation upon substrates 36, with little or no excess fluid which might otherwise be wasted.

Once the nozzle 12 is appropriately charged, its dispensing end 18 may be located adjacent a desired area of the substrate 36 by appropriate positioning of the nozzle 12 and/or the substrate mount 34. The nozzle dispensing end 18 may be situated above the surface of the substrate 36, and the signal generator 26 may be activated to send an appropriate signal via conducting leads 24 to the ultrasonic actuator 22 to cause it to vibrate, preferably at frequencies above 250 kHz and most preferably at frequencies of 500–800 kHz. When using a nozzle 12 formed of a glass pulled pipette having a nozzle interior passage 16 with a diameter of approximately 0.1 micrometers at the nozzle dispensing end 18, excitation at a frequency of 500–800 kHz and an amplitude of 8–10 volts causes fluid in the nozzle to rapidly spray from the nozzle dispensing end 18 onto the substrate 36 as nebulized droplets. When the nozzle 12 is actuated at a lower amplitude (generally 1–4 V, with frequencies again preferably ranging between 500–800 kHz), fluid within the nozzle interior passage 16 does not spray, and instead bulges outwardly to drip or slowly run from the nozzle dispensing end 18, apparently owing to reduced surface tension at the nozzle dispensing end 18 (and possibly also owing to the use of a nozzle 12 having a surface which is at least partly hydrophilic, as where a glass nozzle 12 is used). This form of excitation is useful for producing fluid deposits having particularly regular boundaries when the nozzle dispensing end 18 is positioned upon or very slightly above the surface of the substrate 36.

Temporary excitation of the ultrasonic actuator 22 in the foregoing manner results in the nozzle 12 depositing a spot of fluid on the substrate 36. The size of the deposited fluid spots on the substrate 36 depends primarily on the amount of fluid ejected from the nozzle 12 (which depends in part on how hydrophilic the nozzle 12 is, as well as the frequency, amplitude, and time of ultrasonic actuation), the distance between the nozzle dispensing end 18 and the surface of the substrate 36, and the relative properties of the fluid and the substrate 36 (e.g., the polarity of the deposited fluid relative to the polarity of the material of the substrate 36). Rather than spacing the nozzle dispensing end 18 distantly from the substrate 36 during ejection of fluid, the nozzle 12 may be advanced towards the substrate 36 to such an extent that the nozzle dispensing end 18 contacts or is very closely spaced from the surface of the substrate 36. (As previously noted, advancement of the nozzle 12 onto the surface of the substrate 36 will not result in damage to the nozzle 12 if the nozzle 12 is provided with a flexible mount arrangement, which might be provided by supporting the nozzle 12 solely by use of the flexible conducting leads 24.) This mode of operation, wherein the nozzle dispensing end 18 contacts the substrate 36 or is spaced slightly above it, is particularly useful in cases wherein the substrate 36 is chosen from materials manufactured with greater variation in thickness (such as inexpensive glass slides). Since such materials may have variation in height as great as one micrometer across their areas, it can be difficult to space the nozzle dispensing end 18 at uniform desired heights across the area of the substrate 36 unless sensor feedback is used to assure the desired spacing of the nozzle dispensing end 18 above the substrate 36. However, if the nozzle dispensing end 18 is always made to advance onto the surface of the substrate 36 (with a flexible mounting arrangement for the nozzle 12 avoiding damage to the nozzle dispensing end 18 and substrate 36), the issue of variable spacing between the nozzle dispensing end 18 and substrate 36 is avoided. If the dispensing end 18 is situated on the substrate 36, lower-amplitude excitation of the ultrasonic actuator 22 is preferred so that the fluid simply wicks from the nozzle dispensing end 18 onto the substrate.

Once a first fluid spot is deposited on the substrate 36, the nozzle 12 may be raised by positioning stages 32 and/or 34, indexed to a new position above substrate 36, and a second fluid spot may be deposited in the same manner as the first (provided any fluid is remaining within the nozzle interior passage 16). If the nozzle 12 requires recharging prior to forming a second spot, the nozzle 12 may be indexed back to the first fluid supply well 38 prior to dispensing a second fluid spot on the substrate 36. Alternatively, it may be desirable to have the nozzle 12 dispense a different fluid. In this case, if the nozzle 12 still contains any fluid, it may be indexed by positioning stages 32 and/or 34 to have its dispensing end 18 repositioned above the first fluid supply well 38, and the ultrasonic actuator 22 may be activated to dispense any remaining fluid from within the nozzle interior passage 16 back into the first fluid supply well 38. After (or in place of) this step, the nozzle 12 may be indexed by positioning stages 32 and/or 34 to the rinsing fluid supply well 40 for insertion of the nozzle dispensing end 18 into the well 40. At this time (or after allowing time for uptake of the rinsing fluid within the nozzle interior passage 16 via capillary action), the ultrasonic actuator 22 may be activated to rinse the nozzle 12. Rinsing is preferably performed after the nozzle dispensing end 18 is withdrawn to rest above the rinsing fluid supply well 40 for maximum removal of rinsing fluid from the nozzle 12 and return of the fluid to well 40, though vibrating the nozzle 12 while it is within or being withdrawn from the rinsing fluid supply well 40 is also possible. The vibration beneficially serves to promote fluidization of any materials remaining in the nozzle 12, and thereby promotes thorough cleaning of the nozzle 12 and dispensation of any fluids remaining therein. After rinsing, the nozzle 12 may be indexed to other fluid supply wells containing other fluids desired for dispensation onto the substrate 36, and foregoing steps of charging the nozzle and dispensing the charged fluid onto the substrate 36 may be repeated (with subsequent rinsing steps if desired).

The foregoing processes may be readily automated via the use of computer controls or other programmable logic controls, or even analog-based control systems, to implement the desired nozzle positioning and ultrasonic actuation steps. If desired, positioning sensors, preferably of a laser/optical type, may be used to control the height of the nozzle dispensing end 18 over the substrate 36. Some degree of positioning feedback might also be supplied by monitoring the state of ultrasonic actuator 22 to detect any flexure therein as a result of contact between the nozzle dispensing end 18 and substrate 36, or potentially to detect flexure owing to the weight of fluid within the nozzle 12, though weight detection might be better applied on the leads 24 (or other mount supporting the nozzle 12) at some point distant from the nozzle 12 since the moment forces created by the weight of the charged nozzle 12 will increase with distance from the nozzle 12 and thus might be more easily detected.

The foregoing processes were implemented using a pulled pipette for the nozzle 12, having an inner diameter of approximately 0.1 micrometer at the dispensing end 18. A roughly rectangular slab of diced piezoelectric material was used as the ultrasonic actuator 22. Conductive leads 24 were soldered onto its opposing sides 28 having greatest area. One of its longer edges between these opposing sides 28 was used as its mounting side 30 by bonding this side onto the nozzle outer surface 13 by use of standard isocyanate-based adhesive. When the nozzle was charged with an aqueous test solution such as food coloring and excited at above 250 kHz (preferably at 500–800 kHz), spots on the order of 20 micrometers in diameter were formed on a glass slide substrate situated adjacent to the nozzle dispensing end 18. As previously noted, spot size partially depends on the relative properties of the fluid and the substrate 36, and tests have demonstrated that even smaller spots (on the order of 5 micrometers) may be deposited when an aqueous solution is deposited on a hydrophobic surface. As an example, regular 5 micrometer spots were deposited on the surface of a silicon substrate 36 using an aqueous iron nanoparticle solution. It is notable that the invention's ability to deposit extremely small spots is beneficial not only owing to satisfaction of the need for smaller spot sizes, but also because the ability to dispense very small microvolumes of fluid allows for faster processing speeds in situations where the nozzle 12 is to repeatedly deposit the same fluid (since the nozzle 12 does not need to be recharged with fluid as often as where larger quantities of fluid are dispensed per spot).

It is understood that the various preferred versions of the invention are shown and described above to illustrate different possible features of the invention and the varying ways in which these features may be combined. Apart from combining the different features of the foregoing versions in varying ways, other modifications are also considered to be within the scope of the invention. Following is an exemplary list of such modifications.

Initially, the configurations of the various components of the invention may be changed in numerous respects. As an example, the dispensing nozzle 12 need not have a linear form, e.g., the passage axis of its interior passage 16 need not be linear, and it may instead be curved or bended. Similarly, the ultrasonic actuator 22 may have a wide variety of sizes and configurations (with the rectangular slab actuator 22 shown in FIG. 1 being used merely owing to its easy and inexpensive manufacture), as may the conducting leads 24, which might be defined as planar beams rather than as circular wires so that they might more suitably serve as leaf springs for accommodating flexible mounting of the nozzle 12.

While the foregoing discussion concentrated on the deposition of fluid spots on a substrate 36 (as is useful, e.g., when manufacturing microarrays for biological applications), the invention is not limited to deposition of spots, and lines or other patterns can be "drawn" on a substrate by continuous operation of the ultrasonic actuator 22 during relative motion of the nozzle dispensing end 18 and substrate 36, with the nozzle dispensing end 18 moving with respect to the substrate 36 during fluid dispensation to trace the desired pattern. As an example, the invention may be used in soft lithography applications to draw sub-30 micrometer lines of fluid for use as leads in organic semiconductor chips, organic light emitting diode displays, and similar devices. When drawing continuous features, particularly well-defined lines or patterns may be achieved if the nozzle dispensing end 18 is situated very slightly above the surface of the substrate 36 while the fluid is being dispensed.

Additionally, while the apparatus 10 is depicted with only a single nozzle 12, it is possible to provide several nozzles, each making use of the same or different wells and each depositing fluid on different substrates or on adjacent sections of the same substrate. This measure allows several substrates to be processed at the same time and/or allows several features to be defined on the same substrate at the same time.

While the foregoing discussion primarily relates to the use of the apparatus in a dip-and-dispense methodology (wherein the nozzle 12 is charged by dipping it in an appropriate well), the nozzle 12 could instead be charged via a fluid supply connected to its opposite end 20 (as by a flexible or rigid fluid supply line). In this case, damping caused by the fluid supply line may require modification of the frequency and voltage ranges used to operate the apparatus. Alternatively, nozzle 12 may be inverted from the orientation shown in FIG. 1, the opposite end 20 of a nozzle 12 may rest within the first fluid supply well 38, and the substrate 36 may be situated above the upwardly-facing nozzle dispensing end 18 so that actuation of the ultrasonic actuator 22 directs the fluid from the fluid supply well 38 upwardly onto the substrate 36. While the dip-and-dispense methodology is useful for easily enabling the use of the nozzle 12 with multiple different fluids (with the nozzle being dipped into a desired fluid, the charged fluid being dispensed onto the substrate, and the nozzle then being charged with another fluid), nozzles 12 having attached supply lines at their opposite ends 20 can be made to accommodate different fluids by using a switching/valving arrangement to shift a nozzle's fluid supply line between different fluid supplies (with the flushing of the line and nozzle occurring between each shift if desired). Alternatively or additionally, a nozzle charging methodology using other than capillary action might be implemented, as by applying negative pressure from tubing located at the opposite end 20 of a nozzle 12 to pull fluid into its dispensing end 18, and then using valving or other arrangements to open the tubing to the atmosphere during fluid dispensation so that negative pressure at the opposite end 20 does not interfere with dispensation.

The invention is not intended to be limited to the preferred versions of the invention described above, but rather is intended to be limited only by the claims set out below. Thus, the invention encompasses all different versions that fall literally or equivalently within the scope of these claims.

What is claimed is:

1. A fluid dispensation apparatus comprising:
   a. a nozzle including an outer surface and an interior passage, the interior passage extending between a dispensing end and an opposite end;
   b. an ultrasonic actuator situated on the outer surface of the nozzle and extending from a portion of to outer surface's circumference;
   c. a substrate mount;
   d. one or more conducting leads extending from the ultrasonic actuator, wherein the leads support the nozzle adjacent the substrate mount;
   e. a first fluid supply well wherein a first fluid may be held; and
   f. a positioning stage coupled to the nozzle, the positioning stage allowing the dispensing end of the nozzle to be situated within the first fluid supply well and alternatively adjacent the substrate mount;
   wherein the dispensing end of the nozzle may be situated within the first fluid supply well to charge it with the first fluid, and the dispensing end may then be situated adjacent the substrate mount, whereupon the ultrasonic actuator may be actuated to eject the first fluid from the interior passage of the nozzle and the nozzle's dispensing end toward the substrate mount.

2. The fluid dispensation apparatus of claim 1 further comprising a second fluid supply well containing a rinsing fluid, and wherein the positioning stage allows the dispensing end of the nozzle to be situated within the second fluid supply well.

3. The fluid dispensation apparatus of claim 1 wherein the area of the interior passage at the dispensing end is smaller than the area of the interior passage at the opposite end.

4. The fluid dispensation apparatus of claim 1 wherein the ultrasonic actuator includes opposing sides from which conducting leads extend, and a mounting side therebetween, the mounting side being affixed to the nozzle.

5. The fluid dispensation apparatus of claim 1 wherein the conducting leads are at least partially flexible, whereby the conducting leads may yield when the dispensing end is moved into contact with a substrate.

6. A fluid dispensation apparatus comprising:
   a. a nozzle which circumferentially surrounds an interior passage, the interior passage extending along a passage axis between a dispensing end and an opposite end;
   b. an ultrasonic actuator coupled to a portion of the nozzle's circumference, wherein the ultrasonic actuator includes opposing sides from which conducting leads extend, and a mounting side therebetween, the mounting side being affixed to the nozzle; and
   c. a substrate mount situated adjacent to the dispensing end, wherein:
      (1) the conducting leads support the nozzle adjacent the substrate mount; and
      (2) upon activation of the ultrasonic actuator, fluid resting within the interior passage of the nozzle is ejected from the nozzle's dispensing end toward the substrate mount.

7. The fluid dispensation apparatus of claim 6 wherein the area of the interior passage at the dispensing end is smaller than the area of the interior passage at the opposite end.

8. The fluid dispensation apparatus of claim 6 wherein the conducting leads are at least partially flexible, whereby the conducting leads may yield when the dispensing end is moved into contact with a substrate.

9. The fluid dispensation apparatus of claim 6 wherein:
   a. at least one of the nozzle and the substrate mount is movable with respect to the other of the nozzle and the substrate mount, and
   b. the apparatus further comprises a fluid supply well into which the dispensing end may be inserted to receive fluid.

10. The fluid dispensation apparatus of claim 6 further comprising:
a. a first fluid supply well containing a first fluid;
b. a second fluid supply well containing a rinsing fluid;
c. a positioning stage interposed between:
i. the nozzle, and
ii. the substrate, first fluid supply well, and second fluid supply well,
whereby the positioning stage may adjust the location of the nozzle relative to the substrate, first fluid supply well, and second fluid supply well.

11. A fluid dispensation apparatus comprising:
a. a nozzle which circumferentially surrounds an interior passage, the interior passage extending along a passage axis between a dispensing end and an opposite end;
b. an ultrasonic actuator coupled to a portion of the nozzle's circumference, wherein the ultrasonic actuator has one or more conducting leads extending therefrom; and
c. a substrate mount, wherein the conducting leads support the dispensing end of the nozzle adjacent the substrate mount,
wherein upon activation of the ultrasonic actuator, fluid resting within the interior passage of the nozzle is ejected from the nozzle's dispensing end toward the substrate mount.

12. The fluid dispensation apparatus of claim 11 wherein the conducting leads are at least partially flexible, whereby the conducting leads may yield when the dispensing end is moved into contact with a substrate.

13. The fluid dispensation apparatus of claim 11 wherein the area of the interior passage as the dispensing end is smaller than the area of the interior passage at the opposite end.

14. The fluid dispensation apparatus of claim 11 wherein the ultrasonic actuator includes opposing sides from which conducting leads extend, and a mourning side therebetween, the mourning side being affixed to the nozzle.

15. The fluid dispensation apparatus of claim 11 wherein:
a. at least one of the nozzle and the substrate mount is movable with respect to the other of the nozzle at the substrate mount, and
b. the apparatus further comprises a fluid supply well into which the dispensing end may be inserted to receive fluid.

16. The fluid dispensation apparatus of claim 11 further comprising:
a. a first fluid supply well containing a first fluid;
b. a second fluid supply well containing a rinsing fluid;
c. a positioning stage interposed between:
i. the nozzle, and
ii. the substrate, first fluid supply well, and second fluid supply well,
whereby the positioning stage may adjust the location of the nozzle relative to the substrate, first fluid supply well, and second fluid supply well.

17. A fluid dispensation apparatus comprising:
a. a nozzle which circumferentially surrounds an interior passage, the interior passage extending along a passage axis between a dispensing end and an opposite end;
b. an ultrasonic actuator coupled to a portion of the nozzle's circumference;
c. a substrate mount situated adjacent to the dispensing end;
d. one or more conducting leads extending from the ultrasonic actuator, wherein the leads support the nozzle adjacent the substrate mount;
e. a first fluid supply well containing a first fluid:
f. a second fluid supply well containing a rinsing fluid; and
g. a positioning stage interposed between:
i. the nozzle, and
ii. the substrate, first fluid supply well, and second fluid supply well,
whereby the positioning stage may adjust the location of the nozzle relative to the substrate, first fluid supply well, and second fluid supply well;
wherein upon activation of the ultrasonic actuator, fluid resting within the interior passage of the nozzle is ejected from the nozzle's dispensing end toward the substrate mount.

18. The fluid dispensation apparatus of claim 17 wherein the area of the interior passage at the dispensing end is smaller than area of the interior passage at the opposite end.

19. The fluid dispensation apparatus of claim 17 wherein the ultrasonic actuator includes opposing sides from which conducting leads extend, and a mounting side therebetween, the mounting side being affixed to the nozzle.

20. The fluid dispensation apparatus of claim 17 wherein the conducting leads are at least partially flexible, whereby the conducting leads may yield when the dispensing end is moved into contact with a substrate.

* * * * *